United States Patent [19]

Bindra

[11] 4,329,495

[45] May 11, 1982

[54] ENKEPHALINASE ENZYME INHIBITING COMPOUNDS

[75] Inventor: Jasjit S. Bindra, Groton, Conn.

[73] Assignee: Pfizer Inc., New York, N.Y.

[21] Appl. No.: 264,752

[22] Filed: May 18, 1981

[51] Int. Cl.$^3$ ............................................. C07C 149/41
[52] U.S. Cl. .................................... 562/426; 424/319; 424/324; 564/162
[58] Field of Search .......................... 564/162; 562/426

[56] References Cited

U.S. PATENT DOCUMENTS 4,046,889  9/1977  Ondetti et al. ...................... 424/244

OTHER PUBLICATIONS

Rogues et al., Nature 288,286 (1980).

*Primary Examiner*—Robert Gerstl
*Attorney, Agent, or Firm*—Charles J. Knuth; Albert E. Frost; Robert K. Blackwood

[57] ABSTRACT

Chiral 2-(2-benzyl-3-mercaptopropionylamino)-1-alkanol derivatives and chiral 2-(2-benzyl-3-mercaptopropionylamino)-4-methylthiobutyric acids are inhibitors of enkephalinase enzyme, reflecting their clinical utility as analgesics or anticonvulsant agents, or as therapy for disorders in which endogenous enkephalin levels are below normal.

9 Claims, No Drawings

ENKEPHALINASE ENZYME INHIBITING COMPOUNDS

BACKGROUND OF THE INVENTION

The present invention is concerned with a class of chiral 2-(2-benzyl-3-mercaptopropionyl)amino-1-alkanols, as well as chiral 2-(2-benzyl-3-methylmercaptopropionylamino-4-methylthiobutyric acids, having beneficial CNS (central nervous system) effects including clinical utility as analgesics or anticonvulsants, or as therapy for disorders in which endogenous enkephalin levels are below normal. It is believed that these activities are mediated through the ability of these compounds to inhibit enkephalinase, a dipeptidyl carboxypeptidase which specifically cleaves the $Gly^3$-$Phe^4$ bond of enkephalins. The enkephalins are compounds understood to be signal conveying compounds within the central nervous system. Inhibitors of enkephalins have useful CNS activity.

Roques et al. [Nature 288, pp. 286–288 (1980)] have recently reported that N-(2-benzyl-3-mercaptopropionyl)glycine ("thiorphan") is a specific enkephalinase inhibitor. This compound is reported to elicit analgesic (antinociceptive) activity in mice in the so-called hot plate jump test but not in the so-called tail withdrawal test.

Compounds of the very broad formula

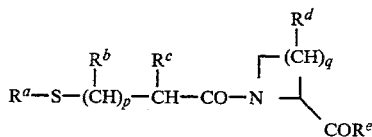

wherein
$R^a$ is H or $R^fCO$;
$R^b$ and $R^c$ are H, alkyl or phenylalkyl;
$R^d$ is H, OH or alkyl;
$R^e$ is OH, alkoxy or $NH_2$;
$R^f$ is alkyl, phenyl or phenylalkyl;
p is 0, 1 or 2; and
q is 1 to 3;

have been reported by Ondetti et al. [U.S. Pat. No. 4,046,889 (July 6, 1977)] as inhibitors of angiotensin converting enzyme, useful as hypotensive agents. Ondetti et al. define a subgenus of "broadly preferred" compounds as including $R^b$ and $R^c$ as other than phenylalkyl and "especially preferred" derivatives are further restricted to proline derivatives (i.e. q=2, $R^d$=H). One compound of this class, having the formula

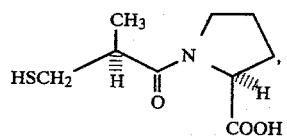

has been assigned the generic name captopril.

SUMMARY OF THE INVENTION

The present invention relates to chiral compounds of the formula

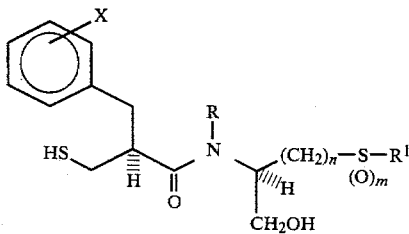

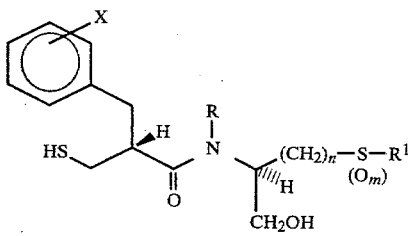

wherein
X is hydrogen, $(C_1$-$C_3)$alkyl, $(C_1$-$C_3)$alkoxy, fluoro, chloro, bromo or trifluoromethyl;
R is hydrogen or $(C_1$-$C_3)$alkyl;
n is 1 to 4;
m is 0, 1 or 2; and
$R^1$ is $(C_1$-$C_3)$alkyl.

Of particular value are the compounds wherein n=2, m=0 and $R^1$=methyl. Within this subgenus, the preferred value of R is hydrogen and the most valued species further have X as p-chloro, p-methoxy or hydrogen.

The present invention also relates to compounds of the formula

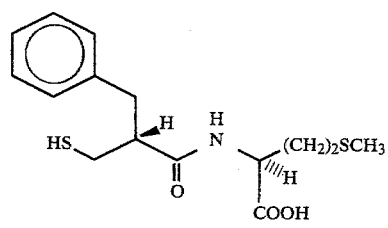

and

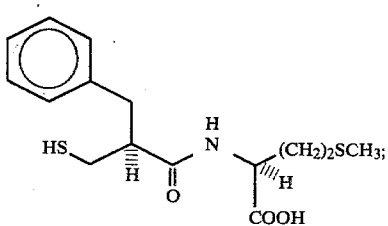

as well as the pharmaceutically acceptable cationic salts thereof. Such salts include the alkali metal salts, e.g., sodium and potassium; alkaline earth metal salts such as calcium and magnesium; aluminum salts; ammonium salts; and salts with organic bases, e.g., amines such as benzathine (N,N'-dibenzylethylenediamine), choline, diethanolamine, ethylenediamine, meglumine (N-methylglucamine), benethamine (N-benzylphenethylamine), diethylamine, piperazine and tromethamine (2-amino-2-hydroxymethyl-1,3-propanediol). Other salts, e.g. the dicyclohexylamine salt, not generally considered to be pharmaceutically acceptable, can also be used for purposes of isolation, purification or testing.

The compounds of the present invention are enkephalinase enzyme inhibitors. It is by this mechanism that these compounds are believed to function as analgesic and anticonvulsant agents in mammals, including man.

Also encompassed by the present invention are methods of alleviating pain (analgesia) or preventing convulsions in a mammal by administering to said mammal and analgesic or an anticonvulsant quantity of a compound of the present invention.

DETAILED DESCRIPTION OF THE INVENTION

The hydroxy compounds of the formulae (I) and (II) are readily prepared by coupling of the appropriate, protected mercapto acid with the appropriate amine, viz.,

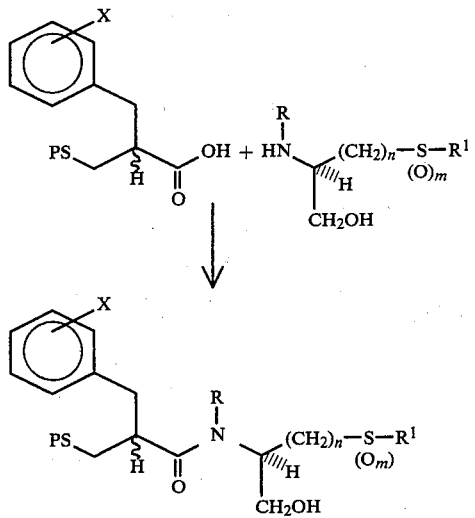

wherein R, X, n, m and $R^1$ are as herein before defined and P is a sulfur protecting group such as benzoyl or acetyl which is selectively removed by a subsequent solvolysis step.

The coupling of the acid with the amine is accomplished by a host of methods well known in the art of peptide chemistry employing essentially molar equivalents of acid and amine so as to maximize yields and minimize possible acylation of the alcohol. In the present instance, a particularly convenient method is to simply convert the acid to acid chloride with an excess of acid chloride forming reagent (e.g. oxalyl chloride, sulfonyl chloride) in an inert, low boiling solvent such as methylene chloride. Temperature is not critical, but temperatures in the range 20°–50° C. are preferred (moderate pressure being required at the upper end of the range if methylene chloride is employed as solvent). The acid chloride is isolated free of solvent and excess reagent by simple evaporation in vacuo, redissolved in an inert solvent and added slowly to a solution of the amino alcohol and at least one molar equivalent of a tertiary amine such as triethylamine or N-methylmorpholine. Temperature again is not critical; for example 0°–50° C. are well suited. Temperatures at the lower end of the range are preferred. If the acid employed in the synthesis is racemic, then it is generally possible to separate the resulting pair of diastereoisomers (epimers) by standard methods of fractional crystallization or chromatography. Alternatively, the diastereoisomers can be separated by the same such methods after removal of the protecting group. When one particular diastereoisomer is desired, it is preferable to use the appropriate chiral acid as the starting material. In any event, the protecting group P is removed selectively by standard solvolytic methods, which generally employ a strong base in water and/or an alcohol, optionally in the presence of a reaction inert, miscible organic solvent. A preferred method is to react the acylthio compound with at least one molar equivalent of sodium methoxide in anhydrous methanol. Generally, no more than a 20% molar excess of the methoxide is used in practice. Temperature is not critical (e.g. 0°–50° C. is well suited); conveniently, ambient temperatures are employed.

The racemic acids required in the above synthesis are readily obtained by condensation of a thiocarboxylic acid with the appropriate 3-phenyl-2-methylenepropionic acid:

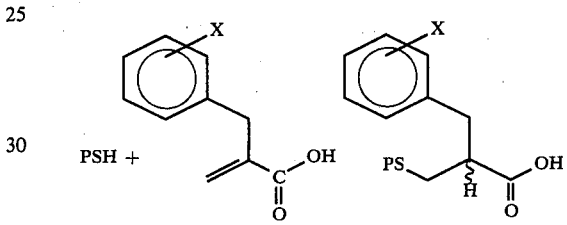

The chiral forms of these acids, when desired, are obtained by forming salts with a chiral amine (e.g. d-(+)-alpha-methylbenzylamine), then employing fractional crystallization techniques well known in the art to separate the diastereomeric salts.

The chiral amino alcohols required for the present syntheses are in many cases commercially available. Alternatively, they are obtained by esterification/hydride reduction of chiral acids/esters available commercially or by literature methods, i.e.:

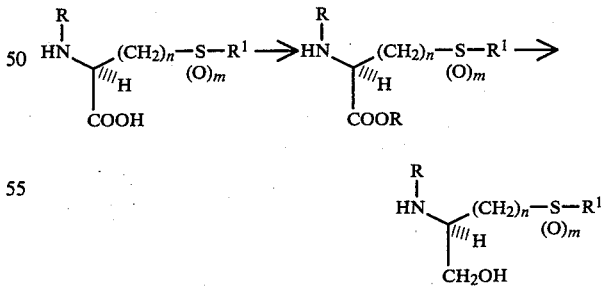

wherein R, n, m and $R^1$ are as defined above. Alternatively the chiral amino alcohol is obtained by standard methods of resolution using a chiral amine at the acid stage, or a chiral acid at the acid, ester or alcohol stage.

The carboxylic acids of the formulae (III) and (IV) are similarly prepared by coupling a protected mercapto acid with L-methionine ester, viz.:

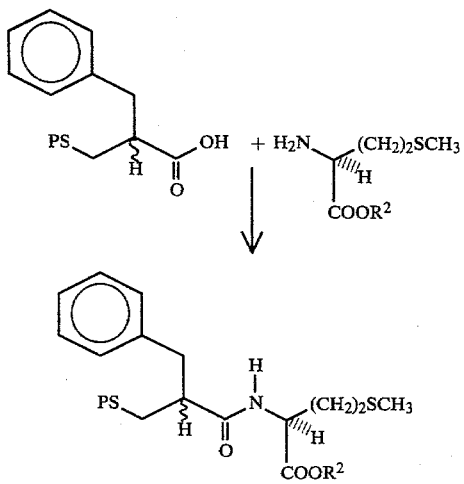

wherein P is as previously defined and $R^2$ is an acid protecting group removable by hydrolysis. The simplest possible ester, i.e. $R^2$=methyl, is perfectly well-suited for the purpose. The coupling is carried out as described above for the coupling of protected mercapto acid with amino alcohols. In this case however, an excess of the acid chloride (or other suitable activated form of the acid) can be used if desired, since no alcohol group is present in the amino ester. Comments presented earlier concerning separation of diastereoisomers, or use of chiral acids as starting materials, apply to this case as well. The protecting groups P and $R^1$ are likewise removed by solvolysis, generally simultaneously by using at least two equivalents of a strong base. One method particularly well suited is to carry out hydrolysis using a small excess of aqueous sodium hydroxide in a water miscible reaction inert solvent, e.g. a lower alcohol, or 1,2-dimethoxyethane.

The pharmaceutically-acceptable cationic salts of the compounds of the formula (III) and (IV) are readily prepared by reacting the acid forms with an appropriate base, usually one equivalent, in a cosolvent. Typical bases are sodium hydroxide, sodium methoxide, sodium ethoxide, sodium hydride, potassium methoxide, magnesium hydroxide, calcium hydroxide, ammonium hydroxide, benzathine, choline, diethanolamine, ethylenediamine, meglumine, benethamine, diethylamine, piperazine and tromethamine. The salt is isolated by concentration to dryness, or by addition of a non-solvent. In some cases, salts can be prepared by mixing a solution of the acid with a solution of a different salt of the cation (e.g. sodium ethylhexanoate, magnesium oleate), employing a solvent in which the desired cationic salt precipitates, or can be otherwise isolated by concentration and/or addition of a non-solvent. When a salt which is not generally considered to be pharmaceutically acceptable is employed for isolation or purification, it can be readily converted to the free acid form by acidification of an aqueous slurry or solution of the salt, extraction into a water immiscible organic solvent and evaporation.

The compounds of the present invention are studied in vitro for inhibition of enkephalinase enzyme in the following manner. To prepare the enzyme, whole brain (minus cerebellum) is removed from Sprague-Dawley CD male rats (Charles River Breeding Laboratories, Inc., Wilmington, MA; 200–250 g.) following decapitation. The tissue is homogenized (Polytron, Brinkmann Instruments, Inc., Westbury, NY) in 30 volumes (w/v) of ice-cold 50 mM Tris-HCl tris(hydroxymethyl)methylamine hydrochloride, Fisher Scientific Co., Fair Lawn, NJ) pH 7.7 buffer. The homogenate in centrifuged at 50,000×g. for 15 minutes. The pellet is resuspended in 50 mM Tris-HCl pH 7.7 buffer and centrifuged at 50,000×g. for 15 minutes. The resultant pellet is resuspended and centrifuged 3 additional times as described above. The membrane pellet is dispersed in 15 volumes of 50 mM Tris-HCl pH 7.7 buffer containing 1% Triton X-100 (Rohm and Haas, Philadelphia, PA) and incubated at 37° C. for 45 minutes. After centrifugation at 100,000×g. for 60 minutes, the solubilized enzymes are frozen in 2 ml. aliquots (this preparation can be stored frozen for 3 months).

To assay inhibitors for inhibition of enkephalinase, triplicate mixtures comprised of 90 microl 50 mM Tris-HCl pH 7.7 buffer containing puromycin dihydrochloride (Sigma Chemical Co., St. Louis, MO), 3.2 mM; 200 microl solubilizing buffer (from final step of enzyme preparation); 5 microl inhibitor (various concentrations, dissolved in water); 200 microl enzyme; and 5 microl $^3$H-leucine-enkephalin (26.8 Ci/mmol, New England Nuclear, Boston, MA), 144 nM, are incubated for 1 hour at 37° C. in 1.8 ml. polyethylene tubes (Beckman Microfuge tubes, Beckman Instruments, Inc., Palo Alto, CA). One set of control tubes contains boiled enzyme (heated at 100° C. for 10 minutes) for blank. The reaction is stopped by boiling tubes for 10 minutes, followed by centrifugation for 1 minute in the Beckman Microfuge centrifuge. A ten microl aliquot of each supernatant is spotted on a thin layer chromatography (TLC) plate (Silica Gel 60, 20×20 cm, E. Merck, Darmstadt, Germany) using 1–8 samples per plate. Ten microl of a standard mixture consisting of 0.4 mg./ml. tyrosine (tyr, Mann Research Laboratories, Inc., New York, NY), 1 mg./ml. L-tyrosylglycine (tyr-gly Sigma), 1 mg./ml. L-tyrosylglycylglycine (tyr-gly-gly, Sigma) and 1 mg./ml. leucine-enkephalin (leu-E, Calbiochem-Behring Corp., La Jolla, CA) are spotted on top of each incubation mixture spot, as well as separately on each plate, to aid in zone indentification.

Plates are dried and placed in covered glass tanks equilibrated with 100 ml. of isopropanol:ethyl acetate:5% acetic acid (2:2:1). After development of the TLC plates, the separated products were visualized by spraying with a ninhydrin:acetone (0.5%, w/v) solution and heating for 10 minutes at 100° C. in a vacuum oven. $R_f$ values of standard markers are: tyr, 0.33; tyr-gly, 0.20: tyr-gly-gly, 0.13; leu-E, 0.47. The radioactive spots are identified by the added markers and scraped into scintillation vials to which 1 ml. ethanol is added, followed by 10 ml. Aquasol-2 (New England Nuclear). Vials are kept overnight and counted for radioactivity in a liquid scintillation counter. Tyr-gly-gly formation is based on the difference between total counts per minute for this TLC zone minus the corresponding value obtained by using boiled enzyme (blank). Activity is reported as the inhibiting molar concentration ($IC_{50}$, M) which will inhibit the enzyme activity to 50% of its normal value. Typical results obtained with various compounds of the present invention are shown in Table I in comparison with thiorphan in the same test.

TABLE I

Enkephalinase Inhibition

| I/II/III/IV | Compound | | | | | $IC_{50}$, M |
|---|---|---|---|---|---|---|
| | X | R | n | m | $R^1$ | |
| I | H | H | 2 | 0 | $CH_3$ | $4.8 \times 10^{-7}$ |
| II | H | H | 2 | 0 | $CH_3$ | $9.6 \times 10^{-6}$ |
| III | — | — | — | — | — | $9.1 \times 10^{-9}$ |
| IV | — | — | — | — | — | $7 \times 10^{-8}$ |
| - Thiorphan - | | | | | | $1.5 \times 10^{-8}$ |

To test for the analgesic activity of the compounds of the present invention, a chemical nociceptive stimulus is employed, viz., blockade of abdominal stretching after phenylbenzoquinone (PBQ). The Carworth CF-1 mouse strain is used, based on the fact that this strain exhibits a particularly clear stretching response. The animals to be used are fasted for 15-16 hr. before the start of the experiment. Fifteen mice (groups of 5) weighing 11-15 g. are employed per dose level. Compounds are given by the oral or subcutaneous route. Drug pre-treatment times are 1 hr. (p.o.) and 20 min. (s.c.). Pairs of mice are injected with 2 mg./kg. of PBQ i.p. and placed in a lucite box (11×7×9.5 in.) maintained at 40° by a thermostatically controlled water bath. Starting 5 min. later the animals are observed for 5 min. and the number of abdominal stretching responses per animal is recorded. A stretch is considered to represent an intermittent contraction of the abdomen, hind limb extension, pelvic rotation, or opisthotonos (the abdomen of the mouse touches the floor of the cage and is dragged the length of the cage). The degree of analgesic protection is calculated on the basis of the suppression of writhing relative to control animals run on the same day (% MPE). Typical results obtained with compounds of the present invention are shown in Table II. This test reflects the ultimate clinical utility of the compounds as analgesic agents.

TABLE II

Percent Blockade of Abdominal Stretching (% MPE) After Phenylbenzoquinone

| I/II/III/IV | Compound | | | | | % MPE | Dose (s.c., mg./kg.) |
|---|---|---|---|---|---|---|---|
| | X | R | n | m | $R^1$ | | |
| I | H | H | 2 | 0 | $CH_3$ | 100 | 320 |
| | | | | | | 69 | 233 |
| | | | | | | 23 | 170 |
| I | 4-$OCH_3$ | H | 2 | 0 | $CH_3$ | 62 | 320 |
| I | 4-Cl | H | 2 | 0 | $CH_3$ | 86 | 320 |
| II | H | H | 2 | 0 | $CH_3$ | (a) | 320 |
| II | 4-$OCH_3$ | H | 2 | 0 | $CH_3$ | 46 | 320 |
| II | 4-Cl | H | 2 | 0 | $CH_3$ | 75 | 320 |
| III | — | — | — | — | — | 57 | 160 |
| IV | — | — | — | — | — | 48 | 160 |

(a) No significant activity noted at this dose level.

The anticonvulsant activity of the compounds of the present invention is determined by testing in mice, viz., Charles River males, Swiss CD strain (17–21 g.), fasted for 18 hr. before testing. Groups of mice are treated with a range of levels of the test compounds, and 1 hr. later with supramaximal electroconvulsive shock (ECS), administered for 0.2 sec. at 50 mA, 60 Hz through transcorneal electrodes. After administration of the electrical stimulus, each mouse is observed for 10 sec. for the presence or absence of hind limb tonic extension. All control mice exhibit such convulsions. Data are summarized in Table III. Blockade of supramaximal ECS in mice is a common laboratory test for clinical utility as an anticonvulsant, and certain known anticonvulsant drugs show activity in this test. It will be further noted that thiorphan was inactive even at a much higher dose.

TABLE III

Anticonvulsant Effect of Enkephalinase Inhibitors vs. Supramaximal Electroconvulsive Shock (ECS) in Mice

| I/II/III/IV | Compound | | | | | $Ed_{50}$ (s.c., mg./kg.) |
|---|---|---|---|---|---|---|
| | X | R | n | m | $R^1$ | |
| I | H | H | 2 | 0 | $CH_3$ | 178 |
| III | — | — | — | — | — | 74.1 |
| IV | — | — | — | — | — | 140.8 |
| - Thiorphan - | | | | | | >320 |

The hydroxy derivatives (formulae I and II), based on the enkephalinase inhibitory and analgesic activities described above, are useful clinically as analgesic agents, i.e., for use in alleviation of pain, while the acid derivatives based on their enkephalinase inhibitory and anticonvulsant activities are useful clinically in preventing convulsions.

In either case, the compounds of the present invention can be formulated in a variety of pharmaceutical preparations which contain the derivative alone or in combination with pharmaceutical carriers such as inert solid diluents, aqueous solutions or various non-toxic, organic solvents and in dosage forms such as gelatin capsules, tablets, powders, lozenges, syrups, injectable solutions and the like. Such carriers include water, ethanol, gelatins, lactose, starches, vegetable oils, petroleum jelly, gums, glycols, talc, benzoyl alcohols, and other known carriers for medicaments. If desired, these pharmaceutical preparations can contain additional material such as preserving agents, wetting agents, stabilizing agents, lubricating agents, absorption agents, buffering agents and isotonic agents.

The derivatives are administered to a patient in need of the particular treatment by a variety of conventional routes of administration such as oral, intravenous, intramuscular or subcutaneous. In general, small doses will be administered initially with a gradual increase in the dose until the optimum level is determined. However, as with any drug the particular dose, formulation and route of administration will vary with the age, weight and response of the particular patient and will depend upon the judgment of his attending physician.

In the usual course of treatment, a total dose of a derivative of approximately 0.1 mg. per day to 100 mg. per day in single or divided doses, will provide effective treatment for the human patient. When the derivative has a prolonged effect, the dose can be administered less frequently, such as every other day or in 1 or 2 divided doses per week.

The present invention is illustrated by the following examples. However, it should be understood that the invention is not limited to the specific details of these examples.

EXAMPLE 1

Methyl 2S-(3-Acetylthio-2R-benzylpropionylamino)-4-methyl-thiobutyrate and

Methyl 2S-(3-Acetylthio-2S-benzylpropionylamino)-4-methyl-thiobutyrate

Thiolacetic acid (10.65 gm., 140.0 mmoles) was added to 2-benzylacrylic acid (10.0 gm., 62.0 mmoles) and the resulting solution was heated at 90° C. under a nitrogen atmosphere for one hour at which time silica gel TLC (ether eluant) indicated that the reaction was essentially complete ($R_f$ 0.3—product; $R_f$ 0.6—starting material). The reaction mixture was cooled and the excess thiolacetic acid was removed under vacuum. The residue was azeotroped once with benzene, triturated three times with hexane and decanted to remove the last traces of thiolacetic acid. The residual red oil was promptly dissolved in methylene chloride (25.0 ml.) and treated with oxalyl chloride (21.8 gm., 170.0 mmoles). The solution was heated at 40° C. in a nitrogen atmosphere for one hour, by which time gas evolution had ceased. The reaction mixture was cooled, evaporated under vacuum and azeotroped once with benzene. The residue was dissolved in methylene chloride (25.0 ml.) and added dropwise over a 0.5 hr. period to a cold (0° C.) stirred mixture of L-methionine methyl ester hydrochloride (12.3 gm., 61.6 mmoles), methylene chloride (75.0 ml.) and triethylamine (14.51 gm., 140.0 mmoles). After the addition was complete, the reaction was stirred for one hour at room temperature under a nitrogen atmosphere, by which time TLC monitoring (ether) indicated the reaction was complete ($R_f$ 0.48, 0.51—products, $R_f$ 0.3—starting material). The reaction was washed with 2 N hydrochloric acid (2×25.0 ml.), water (1×25.0 ml.) and saturated sodium bicarbonate (1×25.0 ml.). The organic layer was dried over anhydrous magnesium sulfate, filtered and concentrated under vacuum to give 25.0 gm. of a mixture of the title products as an oil. The product mixture was separated into two isomers via medium pressure liquid chromatography, using a 7.5 gm. sample mixture and eluting at 35 psi on a 25 mm×1000 mm column with 20% ether/hexane, 25% ether/hexane and 30% ether/hexane. This process was repeated until all of the mixture was separated. There resulted methyl 2S-(3-acetylthio-2S-benzylpropionylamino)-4-methylthiobutyrate: 4.1 gm. (17.3% yield) colorless crystals m.p. 68°–70° C. from ether/hexane (1:1);

Analysis Calcd. for $C_{18}H_{25}O_4NS_2$: C, 56.37; H, 6.57%; N, 3.65. Found: C, 56.19; H, 6.26; N, 3.64.

and methyl 2S-(3-acetylthio-2R-benzylpropionylamino)-4-methylthiobutyrate: 5.4 gm. (22.8% yield) colorless crystals m.p. 65°–7° C. from ether/hexane (1:1).

Analysis Calcd. for $C_{18}H_{25}O_4NS_2$: C, 56.37; H, 6.57; N, 3.65. Found: C, 56.48; H, 6.35; N, 3.68.

By the same procedure 3-acetyl-2R-benzylpropionic acid and 3-acetyl-2R-benzylpropionic acid are reacted with oxalyl chloride and then L-methionine methyl ester to form, respectively, methyl 2S-(3-acetylthio-2R-benzylpropionylamino)-4-methylthiobutyrate and 2S-(3-acetylthio-2S-benzylpropionylamino)-4-methylthiobutyrate, avoiding the need for chromatographic separation of these isomers.

EXAMPLE 2

2S-(2R-Benzyl-3-mercaptopropionylamino)-4-methyl-thiobutyric Acid and 2S-(2S-Benzyl-3-mercaptopropionylamino)-4-methyl-thiobutyric Acid Product mixture of esters of the preceding example (18.82 g., 49.0 mmoles) in 1,2-dimethoxyethane (72.0 ml.) was stirred at room temperature under a nitrogen atmosphere. 2 N Sodium hydroxide (55.0 ml., 110 mmoles) was added and the resulting solution was stirred for one hour, at which time silica gel TLC (9:1 chloroform:ethanol) indicated that the reaction was complete ($R_f$ 0.2—product; $R_f$ 0.75—starting material). 1,2-Dimethoxyethane was removed under vacuum and the residue acidified with 2 N hydrochloric acid to pH 2. The residue was extracted with ethyl acetate (3×100 ml.) and the combined extracts were dried over anhydrous magnesium sulfate. The dried solution was concentrated to give 16.4 gm. of a crude oil product. The oil was chromatographed on 350 gm. silica gel (230–400 mesh) eluting with chloroform then 1% ethanol/chloroform and finally 2% ethanol/chloroform. The product was isolated as a mixture of the two title isomers: 3.4 gm. (21% yield) of a crystalline product, m.p. 130°–2° C. One recrystallization from ethyl acetate gave 2.3 gm. pure product, m.p. 137°–8° C.

Analysis Calcd. for $C_{15}H_{21}O_3NS_2$: C, 55.02; H, 6.46; N, 4.28. Found: C, 54.66; H, 6.18; N, 4.25.

EXAMPLE 3

Dicyclohexylammonium 2S-(2R-Benzyl-3-mercaptopropionylamino)-4-methyl-thiobutyrate A solution of methyl 2S-(3-acetylthio-2R-benzylpropionylamino)-4-methylthio butyrate (0.5 gm., 1.3 mmoles) in 1,2-dimethoxyethane (1.9 ml.) was stirred at room temperature under a nitrogen atmosphere. 2 N Sodium hydroxide (1.3 ml., 2.6 mmoles) was added and the resulting solution was stirred for one hour, with TLC monitoring as in the preceding example. 1,2-Dimethoxyethane was removed under vacuum and the residue acidified with 2 N hydrochloric acid to pH 2. The acidified solution was extracted with ethyl acetate (3×15 ml.) and the combined extracts were dried over anhydrous magnesium sulfate. The dried solution was concentrated to give 484 mg. of a crude oil product. The oil product was converted to the dicyclohexylamine salt in ether to give 479 mg. (72% yield) product, m.p. 152°–5° C. One recrystallization with isopropanol yielded 171 mg. pure product, m.p. 164°–7° C.

Analysis Calcd. for $C_{15}H_{21}O_3N_2S.C_{12}H_{23}N$: C, 63.74; H, 8.72; N, 5.51. Found: C, 63.51; H, 8.35; N, 5.30.

EXAMPLE 4

2S-(2S-Benzyl-3-mercaptopropionylamino)-4-methyl-thiobutyric Acid and

Dicyclohexylamine Salt

By the procedure of the preceding example, methyl 2S-(3-acetylthio-2S-benzylpropionylamino)-4-methyl-thiobutyrate (1 g.) was converted to 939 mg. of the title product as an oil. The oil was chromatographed on 20 gm. of silica gel (230–400 mesh), eluting with ether, to give 716 mg. (84% yield) of pure title product as a clear oil. A 565 mg. sample of the oil was converted to the dicyclohexylamine salt in ether to give 565 mg. product, m.p. 136°–41° C. One recrystallization with benzene yielded 428 mg. product, m.p. 140°–3° C.

Analysis Calcd. for $C_{15}H_{21}O_3N_2S \cdot C_{12}H_{23}N$: C, 63.74; H, 8.72; N, 5.51. Found: C, 63.96; H, 8.58; N, 5.29.

EXAMPLE 5

2S-(3-Benzoylthio-2R-benzylpropionylamino)-4-methylthio-1-butanol and 2S-(3-Benzoylthio-2S-benzylpropionylamino)-4-methylthio-1-butanol A solution of 2-benzyl-3-benzoylthiopropionic acid (4.44 gm., 14.8 mmoles) in methylene chloride (25.0 ml.) was stirred at room temperature under a nitrogen atmosphere. Oxalyl chloride (9.3 gm., 73 mmoles) was added and the resulting solution heated at 40° C. for one hour by which time the evolution of gas ceased. The reaction was cooled, evaporated under vacuum and azeotroped once with benzene to yield the acid chloride. The latter was dissolved in methylene chloride (25.0 ml.) and added dropwise over a 0.5 hr. period to a cold (0° C.) stirred solution of 2S-amino-4-methylthio-1-butanol (2.0 gm., 14.8 mmoles) in methylene chloride (50.0 ml.) and triethylamine (1.65 gm., 16.0 mmoles). After the addition was complete, the reaction was stirred for one hour at room temperature under a nitrogen atmosphere. The reaction was monitored via tlc (silica gel) using 9:1 chloroform:ethanol and after one hour, the reaction was complete ($R_f$ 0.55—products; $R_4$ 0.40—starting material). The reaction was washed with 2 N hydrochloric acid (2×25 ml.), water (1×25.0 ml.) and saturated sodium bicarbonate (1×25.0 ml.). The organic layer was dried over anhydrous magnesium sulfate and concentrated under vacuum to give 5.4 gm. (87% yield) of product, m.p. 95°–7° C. One recrystallization with ethyl acetate gave an analytical sample of the mixed title products melting at 104°–7° C.

Analysis Calcd. for $C_{22}H_{27}O_3NS_2$: C, 63.28; H, 6.52; N, 3.35. Found: C, 63.24; H, 6.32; N, 3.25.

By the same method 2R-benzyl-3-benzoylthiopropionic acid and 2S-benzyl-3-benzoylthiopropionic acid are reacted with oxalyl chloride and then 2S-amino-4-methylthio-1-butanol to yield, respectively, the individual isomeric title products.

By the same method 2-benzyl-3-benzoylthiopropionic acid is reacted with oxalyl chloride and then with 2R-amino-3-methylthio-1-propanol, 2S-amino-5-methylthio-1-pentanol, 2S-amino-6-methylthio-1-hexanol, 2S-amino-4-propylthio-1-butanol, 2S-amino-4-methanesulfinyl-1-butanol and 2S-amino-4-methanesulfonyl-1-butanol to yield respectively:

2R-(3-benzoylthio-2R-benzylpropionylamino)-3-methylthio-1-propanol and 2R-(3-benzoylthio-2S-benzylpropionylamino)-3-methylthio-1-propanol;

2S-(3-benzoylthio-2R-benzylpropionylamino)-5-methylthio-1-pentanol and 2S-(3-benzoylthio-2S-benzylpropionylamino)-5-methylthio-1-pentanol;

2S-(3-benzoylthio-2R-benzylpropionylamino)-6-methylthio-1-hexanol and 2S-(3-benzoylthio-2S-benzylpropionylamino)-6-methylthio-1-hexanol;

2S-(3-benzoylthio-2R-benzylpropionylamino)-4-propylthio-1-butanol and 2S-(3-benzoylthio-2S-benzylpropionylamino)-4-propylthio-1-butanol;

2S-(3-benzoylthio-2R-benzylpropionylamino)-4-methanesulfinyl-1-butanol and 2S-(3-benzylthio-2S-benzylpropionylamino)-4-methanesulfinyl-1-butanol; and 2S-(3-benzoylthio-2R-benzylpropionylamino)-4-methanesulfonyl-1-butanol and 2S-(3-benzylthio-2S-benzylpropionylamino)-4-methanesulfonyl-1-butanol.

EXAMPLE 6

2S-(2R-benzyl-3-mercaptopropionylamino)-4-methylthio-1-butanol and 2S-(2S-benzyl-3-mercaptopropionylamino)-4-methylthio-1-butanol A solution of the mixed title products of the preceding example (4.5 gm., 10.8 mmoles) in anhydrous methanol (50.0 ml.) was stirred at room temperature under a nitrogen atmosphere. Solid sodium methoxide (0.7 gm., 12.96 mmoles) was added portionwise over a ten minute period. The resulting solution was stirred and the reaction monitored via tlc (silica gel) using 9:1 chloroform:ethanol; after one hour the reaction was complete ($R_f$ 0.35, 0.30—products, $R_f$ 0.40—starting material). The reaction mixture was then evaporated under vacuum. The residue was acidified with 2 N hydrochloric acid to pH 2 and extracted with ethyl acetate (3×25.0 ml.). The combined extracts were dried over anhydrous magnesium sulfate and concentrated under vacuum to give 4.98 gm. of a crude oil product mixture. The product mixture was chromatographed on 150 gm. silica gel (230–400 mesh) with chloroform as eluant to give two isomers: 2S-(2R-benzyl-3-mercaptopropionylamino)-4-methylthio-1-butanol, 0.564 gm. (16% yield) colorless crystals m.p. 118°–120° C. from ether/pet. ether;

Analysis Calcd. for $C_{15}H_{23}O_2NS_2$: C, 57.47; H, 7.40; N, 4.47. Found: C, 57.48; H, 7.42; N, 4.52.

and 2S-(2S-benzyl-3-mercaptopropionylamino)-4-methylthio-1-butanol, 0.6 gm. (17% yield) colorless crystals, m.p. 67°–9° C. from ether/hexane.

Analysis Calcd. for $C_{15}H_{23}O_2NS_2$: C, 57.47; H, 7.40; N, 4.47. Found: C, 57.43; H, 7.20; N, 4.42.

Alternatively, the individual title isomers of the preceding example are solvolyzed to yield the individual title isomers of the present example, avoiding the chromatographic separation of isomers.

By the same method the other benzoyl compounds of the preceding example are converted to:

2R-(2R-benzyl-3-mercaptopropionylamino)-3-methylthio-1-propanol and 2R-(2S-benzyl-3-mercaptopropionylamino)-3-methylthio-1-propanol;

2S-(2R-benzyl-3-mercaptopropionylamino)-5-methylthio-1-pentanol and 2S-(2S-benzyl-3-mercaptopropionylamino)-5-methylthio-1-pentanol;

2S-(2R-benzyl-3-mercaptopropionylamino)-6-methylthio-1-hexanol and 2R-(2S-benzyl-3-mercaptopropionylamino)-6-methylthio-1-hexanol;

2S-(2R-benzyl-3-mercaptopropionylamino)-4-propylthio-1-butanol and 2S-(2S-benzyl-3-mercaptopropionylamino)-4-propylthio-1-butanol;

2S-(2R-benzyl-3-mercaptopropionylamino)-4-methanesulfinyl-1-butanol and 2S-(2S-benzyl-3-mercaptopropionylamino)-4-methanesulfinyl-1-butanol; and 2S-(2R-benzyl-3-mercaptopropionylamino)-4-methanesulfonyl-1-butanol and 2S-(2S-benzyl-3-mercaptopropionylamino)-4-methanesulfonyl-1-butanol.

EXAMPLE 7

2S-[3-Benzoylthio-2R-(p-chlorobenzyl)propionylamino]-4-methylthio-1-butanol and

2S-[3-Benzoylthio-2S-(p-chlorobenzyl)propionylamino]-4-methylthio-1-butanol

3-Benzoyl-2-(p-chlorobenzyl)propionic acid (6.34 gm., 18.9 mmoles) and oxalyl chloride (6.5 gm., 4.5 ml., 51.6 mmoles) in 40 ml. of methylene chloride were heated at 40° C. for 1 hour. The reaction mixture was cooled and evaporated to dryness and azeotroped with benzene to yield the corresponding acid chloride. 2S-Amino-4-mercapto-1-butanol (2.56 gm., 18.9 mmoles) and triethylamine (2.76 ml., 19.8 mmoles) were combined in 50 ml. of methylene chloride and cooled to 0° C. The above acid chloride was dissolved in 10 ml. of methylene chloride and added dropwise to the chilled solution. The reaction mixture was warmed to room temperature, stirred for 16 hours, then sequentially washed with two 25 ml. portions of 2 N hydrochloric acid, 25 ml. of water and 25 ml. of saturated sodium bicarbonate, dried over anhydrous magnesium sulfate, filtered, evaporated to dryness, and the residue crystallized with ether to yield 6.69 gm. of the title isomers as a mixture; m.p. 116°–121° C.; ir (KBr) 1645, 1659 cm$^{-1}$. Evaporation of the mother liquor gave an additional 1.6 g. of less pure product.

By the same method 3-benzoyl-2-(m-chlorobenzyl)propionic acid, 3-benzoyl-2-(o-chlorobenzyl)propionic acid, 3-benzoyl-2-(p-fluorobenzyl)propionic acid and 3-benzoyl-2-(p-bromobenzyl)propionic acid are converted, respectively, to:

2S-[3-benzoylthio-2R-(m-chorobenzyl)propionylamino]-4-methylthio-1-butanol and 2S-[3-benzoylthio-2S-(m-chlorobenzyl)propionylamino]-4-methylthio-1-butanol;

2S-[3-benzylthio-2R-(o-chlorobenzyl)propionylamino]-4-methylthio-1-butanol and 2S-[3-benzoylthio-2S-(o-chlorobenzyl)propionylamino]-4-methylthio-1-butanol;

2S-[3-benzylthio-2R-(o-fluorobenzyl)propionylamino]-4-methylthio-1-butanol and 2S-[3-benzoylthio-2S-(o-fluorobenzyl)propionylamino]-4-methylthio-1-butanol; and 2S-[3-benzylthio-2R-(p-bromobenzyl)propionylamino]-4-methylthio-1-butanol and 2S-[3-benzoylthio-2S-(p-bromobenzyl)propionylamino]-4-methylthio-1-butanol.

EXAMPLE 8

2S-[2R-(p-Chlorobenzyl)-3-mercaptopropionylamino]-4-methylthio-1-butanol and

2S-[2S-(p-Chlorobenzyl)-3-mercaptopropionylamino]-4-methylthio-1-butanol

The mixed title compounds of the preceding example (6.67 gm., 14.76 mmole) were solvolyzed according to Example 6, yielding 6.27 g. of a mixture of the title isomeric compounds. The first named of the title isomers (2.0 g.) crystallized directly when the mixture was taken up in ether; m.p. 152°–154° C. Recrystallization from ethyl acetate gave 1.2 g. (m.p. 154°–155° C.) and a second crop of 0.37 g.

Analysis Calcd. for $C_{22}H_{26}O_3ClNS_2$: C, 51.78; H, 6.37; N, 4.03. Found: C, 52.34; H, 6.13; N, 4.01.

The ether mother liquor from the initial crystallization of the first isomer was evaporated to dryness (4.2 g.) and chromatographed on MPLC at 70 psi on a Brinkmann 25×1000 mm column with chloroform as eluant. The second isomeric product fractions were collected and evaporated to dryness. Crystallization from ether gave 0.5 g. of the second named isomer of the title products, m.p. 89°–91° C. Recrystallization from ethyl acetate/hexane gave a 354 mg. first crop (m.p. 90°–92° C.) and 145 mg. second crop.

Analysis Calcd. for $C_{22}H_{26}O_3ClNS_2$: C, 51.78; H, 6.37; N, 4.03. Found: C, 52.06; H, 6.25; N, 4.05.

By the same method the other halo compounds of the preceding example are converted to:

2S-[2R-(m-chlorobenzyl)-3-mercaptopropionylamino]-4-methylthio-1-butanol and 2S-[2S-(m-chlorobenzyl)-3-mercaptopropionylamino]-4-methylthio-1-butanol;

2S-[2R-(o-chlorobenzyl)-3-mercaptopropionylamino]-4-methylthio-1-butanol and 2S-[2S-(o-chlorobenzyl)-3-mercaptopropionylamino]-4-methylthio-1-butanol;

2S-[2R-(p-fluorobenzyl)-3-mercaptopropionylamino]-4-methylthio-1-butanol and 2S-[2S-(p-fluorobenzyl)-3-mercaptopropionylamino]-4-methylthio-1-butanol; and 2S-[2R-(p-bromobenzyl)-3-mercaptopropionylamino]-4-methylthio-1-butanol and 2S-[2S-(p-bromobenzyl)-3-mercaptopropionylamino]-4-methylthio-1-butanol.

EXAMPLE 9

2S-[3-Benzoylthio-2R-(p-methoxybenzyl)propionylamino]-4-methylthio-1-butanol and 2S-[3-Benzoylthio-2S-(p-methoxybenzyl)propionylamino]-4-methylthio-1-butanol 3-Benzoylthio-2-(p-methoxybenzyl)propionic acid (6.6 g., 0.02 mole) was dissolved in 20 ml. of methylene chloride. Oxalyl chloride (4.8 ml., 0.055 mole) was added and the mixture heated at 40° C. for 1 hour. The resulting acid chloride was isolated by evaporation to an oil and azeotroping once with benzene. The acid chloride was redissolved in 10 ml. of methylene chloride and added dropwise to a cold (10° C.) solution of 2S-amino-4-methylthio-1-butanol (2.7 g., 0.02 mole) and triethylamine (3.0 ml., 0.0215 mole) in 30 ml. of methylene chloride. After stirring for 16 hours at room temperature the reaction mixture was sequentially washed with 25 ml. portions of 1 N hydrochloric acid, water and saturated sodium bicarbonate, dried over anhydrous magnesium sulfate, filtered and evaporated to yield 7.1 g. of crude product. The crude was chromatographed by MPLC (silica gel, 25×1000 mm. column, 60 psi) with 10% ethanol in chloroform as eluant to yield a mixture of the title products [4.3 g.; $R_f$ 0.16 (ether); m.p. 88°–92° C.]. The reaction procedure was repeated, except that the crude was triturated with hexane, providing a lower yield (1.88 g., m.p. 84°–87° C.).

By the same method 3-benzoylthio-(p-ethoxybenzyl)propionic acid, 3-benzoylthio-2-(m-isopropylbenzyl)propionic acid, 3-benzoylthio-2-(o-methylbenzyl)propionic acid and 3-benzoylthio-2-(p-trifluoromethylbenzyl)propionic acid are converted, respectively, to:

2S-[3-benzoylthio-2R-(p-ethoxybenzyl)propionylamino]-4-methylthio-1-butanol and 2S-[3-benzoylthio-2S-(p-ethoxybenzyl)propionylamino]-4-methylthio-1-butanol;

2S-[3-benzoylthio-2R-(m-isopropylbenzyl)propionylamino]-4-methylthio-1-butanol and 2S-[3-benzoylthio-2S-(m-isopropylbenzyl)propionylamino]-4-methylthio-1-butanol;

2S-[3-benzoylthio-2R-(o-methylbenzyl)propionylamino]-4-methylthio-1-butanol and 2S-[3-benzoylthio-2S-(o-methylbenzyl)propionylamino]-4-methylthio-1-butanol; and 2S-[3-benzoylthio-2R-(p-trifluoromethylbenzyl)propionylamino]-4-methylthio-1-butanol and 2S-[3-benzoylthio-2S-(p-trifluoromethylbenzyl)propionylamino]-4-methylthio-1-butanol.

EXAMPLE 10

2S-[3-Mercapto-2S-(p-methoxybenzyl)propionylamino]-4-methylthio-1-butanol and

2S-[3-Mercapto-2R-(p-methoxybenzyl)propionylamino]-4-methylthio-1-butanol

The mixed title isomers of the preceding example (5.69 g., 12.7 mmole) were solvolyzed by the procedure of Example 6, yielding 5.9 g. of crude product after evaporation. MPLC on Brinkmann silica gel (230-400 mesh, 25×1000 mm. column) with chloroform as eluant gave the separated title isomers. There resulted pure fractions of the less polar, first named title isomer [1.2 g.; wax; m/e 342; $R_f$ 0.42 (19:1 chloroform:ethanol)], mixed fractions (0.4 g.) and the more polar, second named title isomer [1.2 g.; $R_f$ 0.25 (19:1 chloroform:ethanol); m.p. 130°-134° C.]. The second isomer was recrystallized from ethyl acetate (162 mg., m.p. 138°-140° C.).

Analysis Calcd. for $C_{16}H_{25}NO_3S_2$: C, 55.95; H, 7.34; N, 4.08; m/e 343. Found: C, 56.16; H, 6.89; N, 4.08; m/e 343.

By the same method the other benzoyl compounds of the preceding example are converted to:

2S-[2R-(p-ethoxybenzyl)-3-mercaptopropionylamino]-4-methylthio-1-butanol and 2S-[2S-(p-ethoxybenzyl)-3-mercaptopropionylamino]-4-methylthio-1-butanol;

2S-[2R-(m-isopropylbenzyl)-3-mercaptopropionylamino]-4-methylthio-1-butanol and 2S-[2S-(m-isopropylbenzyl)-3-mercaptopropionylamino]-4-methylthio-1-butanol;

2S-[3-mercapto-2R-(o-methylbenzyl)propionylamino]-4-methylthio-1-butanol and 2S-[3-mercapto-2S-(o-methylbenzyl)propionylamino]-4-methylthio-1-butanol; and 2S-[3-mercapto-2R-(p-trifluoromethylbenzyl)propionylamino]-4-methylthio-1-butanol and 2S-[3-mercapto-2S-(p-trifluoromethylbenzyl)propionylamino]-4-methylthio-1-butanol.

PREPARATION 1 p-Chlorophenylmethylenemalonic Acid

Under nitrogen, malonic acid (powdered, 20 g., 0.192 mole) was mixed with acetyl chloride (15 g., 0.192 mole) and heated to 65° C. in an oil bath. p-Chlorobenzaldehyde (21.6 g., 0.153 mole) was added and the mixture further heated to 80° C. A yellow, slowly refluxing solution resulted, followed by copious precipitation of solids. The mixture was cooled and product recovered by filtration, resuspended in water, stirred for 5 minutes and refiltered to yield title product [21.1 g.; 61% of theory; m.p. 215° C. (dec.)].

By the same method m-chlorobenzaldehyde, o-chlorobenzaldehyde, p-fluorobenzaldehyde and p-bromobenzaldehyde are converted, respectively to:
m-chlorophenylmethylenemalonic acid;
o-chlorophenylmethylenemalonic acid;
p-fluorophenylmethylenemalonic acid; and
p-bromophenylmethylenemalonic acid.

PREPARATION 2 p-Methoxyphenylmethylenemalonic Acid

By the procedure of the preceding preparation, p-methoxybenzaldehyde (21 g., 0.154 mole) was converted to the title product (10.0 g; 58% of theory).

By the same method, p-ethoxybenzaldehyde, m-isopropylbenzaldehyde, o-methylbenzaldehyde and p-trifluoromethylbenzaldehyde are converted to:
p-ethoxyphenylmethylenemalonic acid;
m-isopropylphenylmethylenemalonic acid;
o-methylphenylmethylenemalonic acid; and
p-trifluoromethylphenylmethylenemalonic acid.

PREPARATION 3 p-Chlorobenzylmalonic Acid p-Chloromethylenemalonic acid (71.1 g.) in 600 ml. of ethyl acetate was hydrogenated over 10% Pd/C (3 g.) on a Paar shaker at 50 psig until substantially 1 equivalent of hydrogen was consumed. The catalyst was recovered by filtration and the mother liquor evaporated to dryness in vacuo. The residue was triturated with hexane to yield 69 g. (90%) of the title product.

By the same method the other methylenemalonic acids of Preparation 1 are converted to:
m-chlorobenzylmalonic acid;
o-chlorobenzylmalonic acid;
p-fluorobenzylmalonic acid; and
p-bromobenzylmalonic acid.

PREPARATION 4 p-Methoxybenzylmalonic Acid

The title product of Preparation 2 (15 g.) in 325 ml. of ethyl acetate was hydrogenated over 1 g. of 50% Pd/C according to the preceding example. There resulted 9.8 g. of title product.

By the same method the other methylenemalonic acids of Preparation 2 are converted to:
p-ethoxybenzylmalonic acid;
m-isopropylbenzylmalonic acid;
o-methylbenzylmalonic acid; and
p-trifluoromethylbenzylmalonic acid.

PREPARATION 5

2-(p-Chlorobenzyl)acrylic Acid

The title product of Preparation 3 (35 g., 0.153 mole) was combined with 20 ml. of water, stirred in an ice bath and 25% aqueous dimethylamine was added dropwise to a pH of 7.5. A second portion (35 g.) of the malonic acid was added and sufficient additional water to achieve solution. Aqueous formaldehyde (35 ml. of 36%) was added and the stirred solution allowed to warm gradually to room temperature and stirred for 17 hours. The intermediate dimethylaminomethylated product was recovered by filtration and partially dried by suction (108 g. wet). The wet intermediate was combined with 500 ml. of water and heated on a steam bath for 2 hours, during which the evolution of carbon dioxide was evident. The reaction mixture was cooled, the pH adjusted to 2.0 with 6 N hydrochloric acid and the precipitated title product recovered by filtration (35.3 g., m.p. 95°–96° C.).

By the same method, the other benzylmalonic acids of Preparation 3 are converted to:
2-(m-chlorobenzyl)acrylic acid;
2-(o-chlorobenzyl)acrylic acid;
2-(p-fluorobenzyl)acrylic acid; and
2-(p-bromobenzyl)acrylic acid.

PREPARATION 6

2-(p-Methoxybenzyl)acrylic Acid

The title compound of Preparation 4 (25 g., 0.111 mole) was combined with 25 ml. of water and the pH adjusted to 7.3 with 25% aqueous dimethylamine. The solution was cooled in an ice-acetone bath, additional malonic acid (25 g.) was added and the mixture stirred until solution resulted. Formaldehyde (35 ml. of 36% in water) was added. The mixture was stirred briefly in the ice-acetone bath and then warmed to room temperature. The precipitated title product was recovered by filtration (21 g., 49% of theory).

By the same method, the other benzylmalonic acids of Preparation 4 are converted to:
2-(p-ethoxybenzyl)acrylic acid;
2-(m-isopropylbenzyl)acrylic acid;
2-(o-methylbenzyl)acrylic acid; and
2-(p-trifluoromethylbenzyl)acrylic acid.

PREPARATION 7

3-Benzoylthio-2-(p-chlorobenzyl)propionic Acid

A solution of 2-(p-chlorobenzyl)acrylic acid (3.93 gm., 22 mmoles) and thiobenzoic acid (2.6 ml., 20 mmoles) in 40 ml. of methylene chloride was heated at reflux for 16 hours. The reaction mixture was evaporated to dryness and product crystallized from hexane (4.5 g.). Additional product was obtained by evaporation of the hexane mother liquor and chromatography of the residue (7.1 g.) on 200 g. of silica gel (230-400 mesh) with chloroform as eluant; 1.8 g., m.p. 111°–114° C.

By the same method the other benzylacrylic acids of Preparation 5 are converted to:
3-benzoylthio-2-(m-chlorobenzyl)propionic acid;
3-benzoylthio-2-(o-chlorobenzyl)propionic acid;
3-benzoylthio-2-(p-fluorobenzyl)propionic acid; and
3-benzoylthio-2-(p-trifluoromethylbenzyl)propionic acid.

PREPARATION 8

3-Benzoylthio-2-(p-methoxybenzyl)propionic Acid

By the method of Preparation 7, 2-(p-methoxybenzyl)acrylic acid (3.84 gm., 20 mmoles) was reacted with thiobenzoic acid to yield the title product in essentially quantitative yield [6.61 gm.; $R_f$ 0.48 (ether)].

By the same method, the other benzylacrylic acids of Preparation 6 are converted to:
3-benzoylthio-2-(p-ethoxybenzyl)propionic acid;
3-benzoylthio-2-(m-isopropylbenzyl)propionic acid;
3-benzoylthio-2-(o-methylbenzyl)propionic acid; and
3-benzoylthio-2-(p-trifluoromethyl)propionic acid.

PREPARATION 9

Optical Resolution of 3-benzoylthio-2-benzylpropionic Acid

Racemic 3-benzoylthio-2-benzylpropionic acid (10 g.) was dissolved in 150 ml. of ether and slowly added to 4.24 gm. (35 mmole) of d-(+)-alpha-methylbenzylamine to obtain 14 g. of salt [alpha$_{589}^D$ (C=1, CHCl$_3$)+3.46°]. Two recrystallizations from methylene chloride-hexane furnished 3 gm. of salt containing mostly 2(S) isomer [alpha$_{589}^D$ (C=1, CHCl$_3$)−21.2°]. Further crystallization from isopropyl alcohol gave 1.56 g. of salt of 2(S) isomer [approx. 90% 2(S) isomer], [alpha$_{589}^D$ (C=1, CHCl$_3$)−25°], m.p. 131°–133°. The free acid [approx. 90% 2(S) isomer]was liberated by dissolving in water, adding 2 NHCl, and extracting the product into ethyl acetate. Drying over MgSO$_4$ and concentrating furnished the free 2(S) acid, colorless crystals, m.p. 64°–67°, alpha$_{589}^D$ (C=1, CHCl$_3$)−36.39°.

Coupling with L-methioninol and deprotection afforded predominantly 2S-(2S-benzyl-3-mercaptopropionylamino)-4-methylthio-1-butanol of Example 6.

The pure 2(S)-acid is obtained by further recrystallizations from methylene chloride-hexane or isopropyl alcohol. The corresponding 2(R)-acid can be isolated from mother liquors or by use of 1-(−)-alpha-methylbenzyl amine as the resolving agent.

In like manner other 3-acylthio-2-(substituted-benzyl)propionic acids of preceding examples are resolved into their enantiomers.

I claim:
1. A compound of the formula

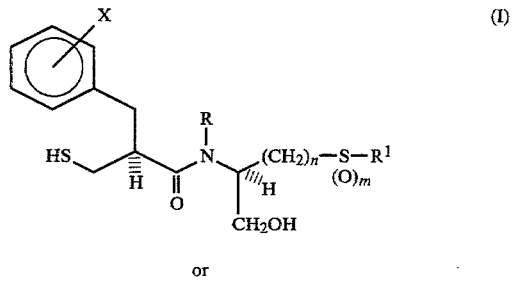

(I)

or

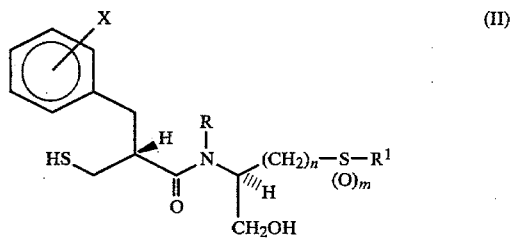

(II)

wherein
X is hydrogen, (C$_1$–C$_3$)alkyl, (C$_1$–C$_3$)alkoxy, fluoro, chloro, bromo, or trifluoromethyl;
R is hydrogen or (C$_1$–C$_3$)alkyl;
n is 1 to 4,
m is 0, 1 or 2; and
R$^1$ is (C$_1$–C$_3$)alkyl.
2. A compound of claim 1 wherein n is 2, m is 0 and R$^1$ is methyl.
3. A compound of claim 2 wherein R is hydrogen.

4. A compound of claim 3 wherein X is p-chloro.
5. A compound of claim 3 wherein X is p-methoxy.
6. A compound of claim 3 wherein X is hydrogen.
7. The compound of claim 6 of the formula (I).
8. The compound of claim 6 of the formula (II).
9. A compound of the formula
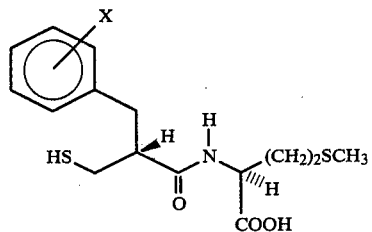
(III)
or
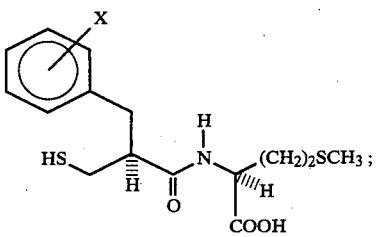
(IV)
or a pharmaceutically acceptable cationic salt thereof.
* * * * *